(12) United States Patent
Dai et al.

(10) Patent No.: US 6,676,954 B2
(45) Date of Patent: Jan. 13, 2004

(54) CONTROLLED RELEASE COMPOSITIONS

(75) Inventors: David Junhui Dai, Lansdale, PA (US); Gary Lewis Willingham, Glenside, PA (US)

(73) Assignee: Rohm and Haas Company, Philadelphia, PA (US)

( * ) Notice: Subject to any disclaimer, the term of this patent is extended or adjusted under 35 U.S.C. 154(b) by 71 days.

(21) Appl. No.: 09/811,760

(22) Filed: Mar. 19, 2001

(65) Prior Publication Data

US 2002/0001618 A1 Jan. 3, 2002

Related U.S. Application Data

(60) Provisional application No. 60/195,147, filed on Apr. 6, 2000.

(51) Int. Cl.[7] .................. A01N 25/00; A01N 25/34; A01N 25/08; A61L 11/00; A61K 31/425
(52) U.S. Cl. .................. 424/405; 424/76.6; 424/76.5; 424/408; 424/409; 424/400; 514/372; 514/373
(58) Field of Search ............. 424/76.6, 76.5, 424/405, 408, 409, 400; 514/372, 373

(56) References Cited

U.S. PATENT DOCUMENTS 5,008,146 A * 4/1991 Keohan ............... 428/328
5,714,137 A * 2/1998 Trinh et al. ............ 424/76.1

FOREIGN PATENT DOCUMENTS

| EP | 106563 | | 4/1984 |
| EP | 0 954 966 | * | 4/1999 |
| EP | 0 922 386 | * | 6/1999 |
| GB | 1113268 | * | 5/1968 |
| JP | 59-227802 | | 12/1984 |
| JP | 63-35504 | | 8/1990 |
| JP | 06-230542 | | 8/1994 |
| JP | 11-116409 | | 4/1999 |
| WO | WO 96/38039 | | 12/1996 |
| WO | WO 00/11949 | | 3/2000 |
| WO | WO 01/14043 | | 3/2001 |

* cited by examiner

*Primary Examiner*—Thurman K. Page
*Assistant Examiner*—Humera N. Sheikh
(74) *Attorney, Agent, or Firm*—Kenneth Crimaldi; Thomas Howell

(57) ABSTRACT

Solid compositions containing low water solubility 3-isothiazolone compounds and carbon-based adsorbents that do not rapidly release the 3-isothiazolone when added to a locus to be protected are disclosed. In particular, methods of controlling or inhibiting the growth of marine organisms using the controlled release solid compositions in paints and coatings for marine structures is disclosed.

10 Claims, No Drawings

CONTROLLED RELEASE COMPOSITIONS

This application claims benefit of 60/195,147 filed Apr. 6, 2000.

BACKGROUND

This invention relates to solid compositions of biocidal compounds that provide controlled release of the biocidal compounds, in particular, the controlled release of certain water-insoluble 3-isothiazolone compounds.

The ability to control the release of 3-isothiazolone compounds to a locus to be protected is important in the field of biologically active compounds, especially in the field of microbicides and marine antifouling agents. Typically, when a 3-isothiazolone compound is added to a locus to be protected, the compound is rapidly released, whether or not it is needed. Controlled release compositions deliver the 3-isothiazolone compound in a manner that more closely matches the need for the compound, that is, only the amount of the 3-isothiazolone compound actually needed is released into the locus to be protected. Controlled release offers the advantages of reduced cost, lowered toxicity and increased efficiency.

Solid formulations of 3-isothiazolone compounds are a useful method of delivering 3-isothiazolone compounds to a locus to be protected. Solid formulations also offer the advantage of safening the 3-isothiazolone compound by reducing the possibility of human exposure. For example, solid compositions eliminate the splash hazard that is common with liquid compositions.

Various solid compositions of 3-isothiazolone compounds are known. Such compositions include encapsulation of the 3-isothiazolone compound, adsorption of the 3-isothiazolone compound on an inert carrier such as silica gel, and clathration of the 3-isothiazolone compound. However, such solid compositions do not always provide controlled release of the 3-isothiazolone compounds. For example, solid compositions where the 3-isothiazolone compound is adsorbed on an inert solid carrier usually do not control the release of the 3-isothiazolone compound. Typically, once such a solid composition is added to a locus to be protected, the 3-isothiazolone compound is rapidly released. Thus, any safening of the 3-isothiazolone compound provided by the solid composition is lost once the composition is added to the locus.

For example, EP 106563 A discloses microbicidal compositions having a water-soluble microbicide admixed with an inert, finely-divided, water-insoluble solid carrier, such as clays, charcoal, inorganic silicates and silicas. These compositions do not provide controlled release of the 3-isothiazolone compounds. The compounds release into the locus by dissolution, and therefore, their release is controlled by the dissolution rate of the particular 3-isothiazolone compound. Similarly, U.S. Pat. No. 4,505,889 discloses microbicidal compositions having microbicide with low water-solubility admixed with an inert, finely-divided, water-insoluble solid carrier, such as clays, inorganic silicates and silicas. JP 63-35504 discloses controlled release sulfonylurea herbicide granules containing a mixture of activated carbon, paraffin wax and mineral based carrier, such as clay or diatomaceous earth. JP 59-227802 discloses an insecticidal resin composition containing an insecticide, a natural or synthetic resin (such as wax, polyethylene or polypropylene) and a porous substance (such as zeolites or activated carbon) to retain the insecticide. WO 96/38039 discloses controlled release pesticide compositions containing activated carbon and adsorbed pesticides, such as insecticides, herbicides or fungicides.

The problem addressed by the present invention is to provide solid compositions of 3-isothiazolone compounds that are safer to handle and provide controlled release of 3-isothiazolone compounds once the composition is added to a locus to be protected.

STATEMENT OF INVENTION

The present invention provides a solid composition comprising a 3-isothiazolone compound having low water solubility and a carbon-based adsorbent, wherein the composition provides controlled release of the 3-isothiazolone compound.

In a preferred embodiment, the invention provides a solid composition wherein the 3-isothiazolone compound is selected from one or more of 2-n-octyl-3-isothiazolone, 4,5-dichloro-2-n-octyl-3-isothiazolone, 4,5-dichloro-2-benzyl-3-isothiazolone and 2-benzyl-3-isothiazolone.

In another aspect, the present invention provides a method for controlling the growth of bacteria, fungi, algae and marine fouling organisms comprising introducing to a locus to be protected the solid composition described above. In particular the invention provides a method for controlling growth of the aforementioned organisms wherein the locus to be protected is selected from one or more of paints, coatings and marine structures.

DETAILED DESCRIPTION

We have discovered that solid compositions useful for providing the controlled release of 3-isothiazolone compounds can be prepared by combining selected 3-isothiazolone compounds having low water solubility with a carbon-based adsorbent. In particular, we have discovered that specific 3-isothiazolones combined in specific relative proportions with carbon-based adsorbents unexpectedly provides the controlled release compositions of the present invention.

As used throughout the specification, the following terms shall have the following meanings, unless the context clearly indicates otherwise. "Microbicide" refers to a compound capable of inhibiting the growth of or controlling the growth of microorganisms in a locus. The term "locus" does not include pharmaceutical or veterinary applications. The term "microorganism" includes, for example, fungi, bacteria and algae. "Marine antifouling agent" includes algaecides and molluscicides. "Marine antifouling activity" is intended to include the elimination of and inhibition of growth of marine organisms. Marine organisms controlled by marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges and anemones; and the term "hard fouling organisms" refers to invertebrates having some type of hard outer shell, such as barnacles, tubeworms and molluscs.

As used herein, the term "low water solubility," as applied to the 3-isothiazolones, means that the 3-isothiazolone is characterized by having a water solubility of less 1000 ppm (0.1%), preferably less than 500 ppm (0.05%) and more preferably less than 100 ppm (0.01%).

Unless otherwise specified, ranges listed are to be read as inclusive and combinable, temperatures are in degrees centigrade (° C.) and references to percentages (%) are by weight. As used throughout this specification, the following abbreviations are applied: g=grams, mL=milliliter, ppm=parts per million (weight/weight) and mm=millimeter.

Suitable 3-isothiazolones useful in the present invention are those isothiazolones having low water solubility and are represented by the formula:

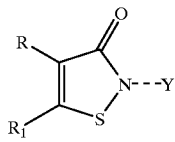

(I)

wherein:
Y is an unsubstituted or substituted ($C_7$–$C_{18}$)alkyl group, an unsubstituted or substituted ($C_7$–$C_{18}$)alkenyl or alkynyl group, an unsubstituted or substituted ($C_7$–$C_{12}$) cycloalkyl group, an unsubstituted or substituted ($C_7$–$C_{10}$)aralkyl group, or a substituted ($C_7$–$C_{10}$)aryl group;

R and $R_1$ are independently hydrogen, halogen or ($C_1$–$C_4$) alkyl groups; or R and $R_1$ can be taken together with the C=C double bond of the isothiazolone ring to form an unsubstituted or substituted benzene ring.

By a "substituted alkyl group" is meant an alkyl group having one or more of its hydrogens replaced by another substituent group; examples include hydroxyalkyl, haloalkyl and alkylamino. By a "substituted aralkyl group" is meant an aralkyl group having one or more of its hydrogens on either the aryl ring or the alkyl chain replaced by another substituent group; examples include halo, ($C_1$–$C_4$)alkyl, halo-($C_1$–$C_4$)alkoxy and ($C_1$–$C_4$)alkoxy. By a "substituted aryl group" is meant an aryl group, such as phenyl, naphthyl or pyridyl groups, having one or more of its hydrogens on the aryl ring replaced by another substituent group; examples include halo, nitro, ($C_1$–$C_4$)alkyl, halo-($C_1$–$C_4$)alkoxy and ($C_1$–$C_4$)alkoxy.

Suitable 3-isothiazolone compounds include, for example, 2-n-octyl-3-isothiazolone, 4,5-dichloro-2-n-octyl-3-isothiazolone, 4,5-dichloro-2-benzyl-3-isothiazolone, 2-benzyl-3-isothiazolone and 2-haloalkoxyaryl-3-isothiazolones (such as 2-(4-trifluoromethoxyphenyl)-3-isothiazolone, 2-(4-trifluoromethoxyphenyl)-5-chloro-3-isothiazolone and 2-(4-trifluoromethoxyphenyl)-4,5-dichloro-3-isothiazolone). Preferably, the 3-isothiazolone is selected from one or more of 2-n-octyl-3-isothiazolone and 4,5-dichloro-2-n-octyl-3-isothiazolone.

When the 3-isothiazolone compound is a solid, the compositions of the invention may be prepared by mixing the 3-isothiazolone compound, as a melt or as a solution, with the carbon-based adsorbent. When the 3-isothiazolone compound is a liquid, the 3-isothiazolone compound may be mixed "as is" with the carbon-based adsorbent, or mixed as a solution with the carbon-based adsorbent. Suitable solvents for the 3-isothiazolone compound are any which dissolve the compound, do not destabilize it and do not react with the carbon-based adsorbent. Suitable solvents include alcohols, such as methanol, ethanol and propanol; esters, such as ethyl acetate and butyl acetate; ketones, such as acetone and methyl iso-butyl ketone; and nitriles, such as acetonitrile. Preferred solvents are ($C_1$–$C_4$)alcohols.

The total amount of 3-isothiazolone compound in the composition is 0.1 to 95%, based on the combined weight of the carbon-based adsorbent and the 3-isothiazolone compound. Preferably, the total amount of 3-isothiazolone compound is 1 to 50% and more preferably 5 to 30%. Thus, the weight ratio of 3-isothiazolone compound to carbon-based adsorbent in the compositions is generally from 0.1:99.9 to 95:5, preferably from 1:99 to 50:50 and more preferably from 5:95 to 30:70.

Suitable carbon-based adsorbents include, for example, carbons such as those derived from coal, wood, coconut shells, lignin or animal bones; carbon blacks such as those derived from gas phase pyrolysis of hydrocarbons; natural or synthetic graphites or graphite whiskers; cokes such as those obtained from the destructive distillation of bituminous coal, petroleum and coal-tar pitch; high surface area activated carbons; and pyrolyzed carbonaceous adsorbents prepared by pyrolysis of resinous polymers (such as Ambersorb™ carbonaceous adsorbents, available from Rohm and Haas Company, Philadelphia, Pa.; see *Carbonaceous Adsorbents for the Treatment of Ground and Surface Waters*, J. W. Neely and E. G. Isacoff, Vol 21 of Pollution Engineering and Technology Series, Marcel Dekker, Inc., New York, N.Y., pp 41–78 (1982), for further general and specific details on pyrolyzed carbonaceous adsorbents and their method of preparation). Preferably the carbon-based adsorbent is selected from one or more of activated carbon and pyrolyzed carbonaceous adsorbent.

Particularly preferred are high surface area "activated" carbons, such as those prepared by direct chemical activation. *Petroleum Derived Carbons* (by T. M. O'Grady and A. N. Wennerberg), American Chemical Society Symposium Series, Vol. 303, J. D. Bacha et al., eds., American Chemical Society Publications, Washington, D.C., (1986), may be consulted for further general and specific details on these activated carbons and their method of preparation.

The carbon-based adsorbents are typically particulate materials having an average particle size of 0.01 to 5 mm (10 to 5000 microns), preferably from 0.02 to 2 mm and more preferably from 0.1 (less than 100 mesh) to 1 mm (about 18 mesh). When relatively large particle sized carbon-based adsorbents are used, the average particle size typically ranges from 0.5 to 3 mm, preferably from 1 to 2 mm (greater than 18 mesh) and more preferably from 1.5 to 2 mm. When smaller particle sized carbon-based adsorbents are used, the average particle size typically ranges from 0.02 to 0.3 mm and preferably from 0.03 to 0.15 mm (30 to 150 microns, less than 100 mesh).

More than one 3-isothiazolone compound may be used in the compositions of the present invention as long as the compounds do not react with, or otherwise destabilize, each other and are compatible with the carbon-based adsorbent. This has the advantage of safening multiple 3-isothiazolone compounds which may provide a broader spectrum of control than one compound used alone.

The compositions of the present invention are useful wherever the low water solubility 3-isothiazolone compound would be useful. The compositions are suitable for use in any locus requiring protection from microorganisms. Suitable loci include, for example, cooling towers; air washers; mineral slurries; pulp and paper processing fluids; paper coatings; swimming pools; spas; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood products, including lumber, timber, fiberboard, plywood, and wood composites; plastics; lubricants; hydraulic fluids; medical devices; metalworking fluids; emulsions and dispersions; paints, including marine paints; varnishes, including marine varnishes; latexes; odor control fluids;

coatings, including marine coatings; petroleum processing fluids; fuel; oil field fluids; photographic chemicals; printing fluids; sanitizers; detergents; textiles; textile products; and marine structures. Preferably the locus to be protected is selected from one or more of paints, coatings and marine structures.

The compositions of the present invention can either be added directly to the locus to be protected or added as a composition further comprising a suitable carrier. Suitable carriers include, for example, water, acetonitrile, ethyl acetate, butyl acetate, toluene, xylene, methanol, ethanol, acetone, methyl ethyl ketone, methyl isobutyl ketone, methyl isoamyl ketone, ethylene glycol, diethylene glycol, propylene glycol and dipropylene glycol. When the compositions of the present invention are used in marine antifoulant formulations, the compositions preferably incorporate an optional carrier selected from one or more of water, xylene, methyl isobutyl ketone and methyl isoamyl ketone. The compositions may also be formulated as microemulsions, microemulsifiable concentrates, emulsions, emulsifiable concentrates, pastes, or may be encapsulated. The particular formulation will depend upon the locus to be protected and the particular low water solubility 3-isothiazolone used. The preparation of these formulations are by well known, standard methods.

The amount of the compositions of the invention necessary to control or inhibit the growth of microorganisms depends upon the locus to be protected, but is typically sufficient if it provides 0.1 to 5000 ppm of 3-isothiazolone at the locus to be protected. 3-Isothiazolones are often used in loci that require further dilution. In a locus such as a paint, which is not further diluted, the amount of the compositions of the invention necessary to control microorganism growth are sufficient if they provide generally 200 to 5000 ppm of the 3-isothiazolone.

When the low water solubility 3-isothiazolone compound of the present invention is used in a marine antifoulant formulation, that is, as a marine antifouling agent, the compositions of the present invention can be used to inhibit the growth of marine organisms by application of the compositions onto or into a marine structure. Depending upon the particular marine structure to be protected, the compositions of the present invention can be directly incorporated into the marine structure, applied directly to the marine structure, or incorporated into a coating which is then applied to the marine structure.

Suitable marine structures include, but are not limited to: boats, ships, oil platforms, piers, pilings, docks, elastomeric rubbers, and fish nets. The compositions of the present invention are typically directly incorporated into structures such as elastomeric rubber or fish net fibers during manufacture. Direct application of the compositions of the invention is typically made to structures such as fish nets or wood pilings. The compositions of the invention can also be incorporated into a marine coating, such as a marine paint or varnish.

Optionally, the controlled release compositions of the present invention may include other marine antifouling agents in addition to the low water solubility 3-isothiazolones. Suitable optional marine antifouling agents useful in the present invention include, for example, manganese ethylenebisdithiocarbamate, zinc ethylenebisdithiocarbamate, zinc dimethyl dithiocarbamate, 2-methylthio-4-t-butylamino-6-cyclopropylamino-s-triazine, 2,4,5,6-tetrachloroisophthalonitrile, 3-(3,4-dichloro-phenyl)-1,1-dimethyl urea, zinc ethylenebisdithiocarbamate, copper thiocyanate, N-(fluorodichloromethylthio)phthalimide, N,N-dimethyl-N'-phenyl-N'-fluorodichloromethylthiosulfamide, zinc 2-pyridinethiol-1-oxide, copper 2-pyridinethiol-1-oxide, tetramethylthiuram disulfide, 2,4,6-trichlorophenylmaleimide, 2,3,5,6-tetrachloro-4-(methylsulfonyl)pyridine, 3-iodo-2-propynylbutylcarbamate, diiodomethyl p-tolyl sulfone, bis dimethyl dithiocarbamoyl zinc, phenyl (bispyridil) bismuth dichloride, 2-(4-thiazolyl)-benzimidazole, pyridine triphenyl borane, phenylamides and halopropargyl compounds.

Additional optional compounds that may be incorporated into the solid controlled release compositions of the present invention include, for example, 2-($C_1$–$C_6$)alkyl-3-isothiazolones (such as 2-methyl-3-isothiazolone and 5-chloro-2-methyl-3-isothiazolone) and 2-phenyl-3-isothiazolone.

When the solid compositions of the present invention are used in marine antifoulant formulations, the amount of the compositions necessary to inhibit or prevent the growth of marine organisms is typically sufficient if it provides from 0.1 to 30%, preferably from 0.5 to 20% and more preferably from 1 to 10%, of the low water solubility 3-isothiazolone, based on the weight of the structure to be protected or based on the weight of the coating to be applied (whether directly incorporated into or directly applied onto a structure). In the case of a marine antifouling paint, the concentration of low water solubility 3-isothiazolone is typically from 0.1 to 15%, preferably from 0.2 to 5% and more preferably from 0.5 to 3%, based on total weight of the paint formulation.

In general, the compositions of the present invention may be used by first forming the solid composition (combining the low water solubility 3-isothiazolone with a carbon-based adsorbent), followed by addition of the solid composition to various loci (as previously described).

Alternatively, the present invention may be practiced, in particular for controlling the growth of bacteria, fungi, algae and marine fouling organisms, by introducing to any locus to be protected: (a) a carbon-based adsorbent, and (b) a low water solubility 3-isothiazolone compound as represented by formula I. For example, when the locus is a solvent-based paint, such as a marine antifouling paint, the paint formulation may be prepared by adding the carbon-based adsorbent and 3-isothiazolone separately, and in any order, to the base paint formulation.

Direct applications of the compositions of the present invention may be by any conventional means, such as dipping, spraying or coating. Fish nets, for example, may be also protected by dipping the fish nets into a composition comprising the compositions of the invention and a carrier or by spraying the fish nets with the composition.

Structures such as wood pilings and fish nets may be protected by directly incorporating the compositions of the invention into the structure. For example, a composition of the invention further comprising a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The compositions of the invention are suitable for use in both solvent and water based marine coatings. Solvent based marine coatings are preferred.

Any conventional binder may be utilized in the marine antifouling coating incorporating the compositions of the invention. Suitable binders include, for example, polyvinyl chloride in a solvent based system, chlorinated rubber in a solvent based system, acrylic resins in solvent based or aqueous systems, vinyl chloride-vinyl acetate copolymer systems as aqueous dispersions or solvent based systems, butadiene-styrene rubbers, butadiene-acrylonitrile rubbers, butadiene-styrene-acrylonitrile rubbers, drying oils such as linseed oil, asphalt, epoxies, siloxanes and silicones.

The marine coatings of the present invention may optionally contain one or more of the following: inorganic pigments, organic pigments or dyes, and natural resins, such as rosin. Water based coatings may also optionally contain: coalescents, dispersants, surface active agents, rheology modifiers or adhesion promoters. Solvent based coatings may also optionally contain extenders, plasticizers or rheology modifiers.

A typical marine coating comprises 2 to 20% binders, up to 15% rosins/modified rosins, 0.5 to 5% plasticizers, 0.1 to 2% antisettling agent, 5 to 60% solvent/diluent, up to 70% cuprous oxide, up to 30% pigments (other than cuprous oxide) and up to 15% marine antifouling agent (in this case, low water solubility 3-isothiazolone).

Marine coatings containing the compositions of the invention may be applied to a structure to be protected by any of a number of conventional means, such as, for example, spraying, rolling, brushing and dipping.

Some embodiments of the invention are described in detail in the following Examples. All ratios, parts and percentages (%) are expressed by weight unless otherwise specified, and all reagents used are of good commercial quality unless otherwise specified.

EXAMPLE 1

The controlled release compositions of the invention were prepared by the following general method.

To 1.0 g of activated carbon (as the carbon-based adsorbent) in a flask was added 2.1 g of a 20% solution of 4,5-dichloro-2-n-octyl-3-isothiazolone in methanol. The resulting slurry was then dried under reduced pressure at 55° C. to yield about 1.4 g of a dark powder. This composition, designated as Sample 1-1, contained 30% of 4,5-dichloro-2-n-octyl-3-isothiazolone based on the total weight of the powder. In similar fashion, 3-isothiazolone/activated carbon powders were prepared corresponding to 30% active ingredient (3-isothiazolone)/70% activated carbon. Compositions are summarized in Table 1.

TABLE 1

3-Isothiazolone (30%)/Activated Carbon (70%) Compositions

| Sample | 3-Isothiazolone Component |
|---|---|
| 1-1 | 4,5-dichloro-2-n-octyl-3-isothiazolone |
| 1-2 | 2-n-octyl-3-isothiazolone |
| 1-3* | 2-methyl-3-isothiazolone |
| 1-4* | 5-chloro-2-methyl-3-isothiazolone |
| 1-5* | 4,5-dichloro-2-cyclohexyl-3-isothiazolone |

* = comparative

EXAMPLE 2

The amount of 3-isothiazolone compound released from each controlled release composition was determined according to the following general procedure. A weighed amount of controlled release composition (0.014 g, prepared as described in Example 1) was placed in a 250 mL sample jar. To the jar was then added 200 mL of water containing 0.3% of sodium diethylhexylsulfosuccinate. The solution was then gently stirred to ensure no foam was formed. Aliquots (0.5 mL) were taken at 5 and 24 hours and transferred to a microcentrifuge tube. Each aliquot was then centrifuged at 14,000 rpm for 3 minutes. The supernatant was then removed and analyzed by HPLC (high pressure liquid chromatography) for the amount of the 3-isothiazolone compound. The microcentrifuge tube was then washed with 0.5 mL of water containing 0.3% of sodium diethylhexylsulfosuccinate and the wash liquid added to the sample jar. This ensured that none of the particles removed during sampling was lost and that the volume in the jar remained constant. The cumulative percentages of 3-isothiazolone released are reported in Table 2.

TABLE 2

| | Relative % 3-Isothiazolone Released | |
|---|---|---|
| Sample | 5 Hours | 24 Hours |
| 1-1 | 0.0 | 0.0 |
| 1-2 | 0.0 | 5 |
| 1-3* | 76 | 86 |
| 1-4* | 38 | 52 |
| 1-5* | 100 | — |

* = comparative

The above data clearly show that the 3-isothiazolone compositions containing 4,5-dichloro-2-n-octyl-3-isothiazolone and 2-n-octyl-3-isothiazolone greatly control the release of the 3-isothiazolone compound as compared to the compositions containing the more water-soluble 3-isothiazolones (2-methyl-3-isothiazolone, 5-chloro-2-methyl-3-isothiazolone and 4,5-dichloro-2-cyclohexyl-3-isothiazolone).

EXAMPLE 3

The efficacy of the 3-isothiazolone/carbon-based adsorbent compositions of the present invention in a paint film was determined by a salt water (synthetic-seawater) leaching evaluation. An appropriate amount of 4,5-dichloro-2-n-octyl-3-isothiazolone (ITA), together with carbon-based adsorbent (C-1, C-2, C-3):

C-1=Darco™ G-60 (−100 mesh, from Aldrich Chemical Company)

C-2=Activated Carbon (6–14 mesh, from Fisher Scientific)

C-3=Carbon Black (Raven™ 3500, beads, from Columbia Chemicals), was added to 10 g of a marine antifouling paint formulation (2 different paint types, P-1 and P-2, see below) in a milling jar to provide a final 3-isothiazolone concentration of 2% based on total combined weight of the 3-isothiazolone/carbon-based adsorbent/paint formulation mixture. Paint films were then drawn on silanized microslides to a thickness of 0.076 mm (0.003 inch) for the rosin-based paint formulation (P-1) and to a thickness of 0.178 mm (0.007 inch) for the polishing type marine antifouling paint (P-2). The paint films were dried for 2 days and then the microslides were placed in a synthetic-seawater fish tank for 1 month. The synthetic-seawater was periodically circulated through a filter cartridge containing activated carbon and Celex™ 20 chelating agent (to remove 3-isothiazolone and copper ions). At various times the paint slides were removed and analyzed. The amount of 4,5-dichloro-2-n-octyl-3-isothiazolone remaining in the paint film after exposure to synthetic-seawater was determined by radioactive labeling ($^{14}$C-labeled 4,5-dichloro-2-n-octyl-3-isothiazolone).

| Composition of Rosin-Based Paint (P-1): | |
|---|---|
| 5% | Cellolyn ™ 102M (rosin) |
| 15% | Laroflex ™ MP-45 (binder resin) |
| 39% | Cuprous oxide |
| 19% | Xylene |
| 19% | Methyl isobutyl ketone |
| 2% | Tritolyl (tricresyl) phosphate |
| 1% | Bentone ™ 38 (clay) |
| Composition of Polishing Type Marine Antifouling Paint (P-2): | |
| 20–50% | Tributyl tin (meth)acrylate copolymer |
| 25–60% | Cuprous oxide |
| 10–25% | Xylene (+ other solvents) |
| 5–15% | Additives (plasticizers, settling aids, fillers) |

The salt water leaching test and radioactive labeling measurements were conducted as follows: a small amount of $^{14}C$-4,5-dichloro-2-n-octyl-3-isothiazolone was incorporated with $^{12}C$-4,5-dichloro-2-n-octyl-3-isothiazolone into paint and the radioactivity of trace $^{14}C$-molecules was measured by a Phosphorimager SI spectrometer (manufactured by Molecular Dynamics Co.); a ratio of $4 \times 10^{-5}$ for $^{14}C$-4,5-dichloro-2-n-octyl-3-isothiazolone to every gram of $^{12}C$-4,5-dichloro-2-n-octyl-3-isothiazolone was used. The use of $^{14}C$-4,5-dichloro-2-n-octyl-3-isothiazolone as trace molecules did not affect the total active ingredient level in the paint.

The prepared slides were placed in synthetic-seawater prepared as follows: the following ingredients (20 liters deionized water, 1350 g NaCl, 225 g $MgCl_2 \cdot 6H_2O$, and 321.6 g $Na_2B_4O_7 \cdot 10H_2O$ in 6 liters deionized water) were combined and adjusted to a pH of 8.2 with 1.0 M HCl solution, after which the total volume was made up to 30 liters with additional deionized water.

The % retention of the 3-isothiazolone in the various formulations is summarized in Table 3.

TABLE 3

% 4,5-Dichloro-2-n-octyl-3-isothiaolone (ITA) Retained in Paint Film

| Carbon Type | Paint Type | Ratio of ITA/carbon | 0 Days | 7 Days | 14** Days | 21 Days | 30 Days |
|---|---|---|---|---|---|---|---|
| C-1 | P-2 | 20/80 | 100 | 94 | (89) | 84 | 83 |
| C-1 | P-2 | 40/60 | 100 | 67 | (57) | 47 | 42 |
| C-1 | P-2 | 60/40 | 100 | 60 | (47) | 35 | 29 |
| C-1 | P-2 | 80/20 | 100 | 50 | (37) | 24 | 19 |
| C-2 | P-2 | 20/80 | 100 | 97 | (96) | 94 | 96 |
| C-2 | P-2 | 30/70 | 100 | 91 | 85 | — | — |
| C-2 | P-2 | 40/60 | 100 | 70 | (62) | 54 | 50 |
| C-2 | P-2 | 60/40 | 100 | 57 | 48 | 37 | 33 |
| C-2 | P-2 | 80/20 | 100 | 54 | 41 | 29 | 24 |
| C-3 | P-2 | 30/70 | 100 | 58 | 42 | — | — |
| C-3 | P-2 | 60/40 | 100 | 58 | 41 | — | — |
| None | P-2 | 100/0 | 100 | 31–44* | 20–(30)* | 18 | 13 |
| C-1 | P-1 | 30/70 | 100 | 91 | (89) | — | 84 |
| C-2 | P-1 | 30/70 | 100 | 98 | (97) | — | 96 |
| None | P-1 | 100/0 | 100 | 82 | (78) | — | 70 |

\* = range for 2 separate determinations
\*\* = values in () are interpolated

The above data demonstrate that the activated carbon compositions (C-1 and C-2) control the release of 4,5-dichloro-2-n-octyl-3-isothiazolone to a greater degree than the carbon black composition; however, both activated carbon and carbon black compositions provide significant retention of the ITA in the paint film relative to the compositions ("None") containing no carbon at all. The two types of paint formulations provide different baseline performance characteristics for the retention of the ITA without any carbon-based adsorbent present; data may be compared only within each type of paint formulation. At the preferred loading levels of ITA relative to the activated carbon materials, that is, less than 50:50, the ITA retention values consistently exceed 50% at the 14 day point for the P-2 type paint formulation.

EXAMPLE 4

The efficacy of other types of carriers besides carbon-based adsorbents in the low water solubility 3-isothiazolone/carrier compositions was determined for comparative purposes:

C-1=Activated Carbon (Darco™ G-60, 100 mesh)
C-4=Diatomaceous earth (Celite™ 545)
C-5=Aluminosilicate (kaolin clay)
C-6=Magnesium silicate (talc)

The carriers were loaded with 30% 4,5-dichloro-2-n-octyl-3-isothiazolone by combining the appropriate amounts of carrier with a 20% solution of 4,5-dichloro-2-n-octyl-3-isothiazolone (in methanol) in a round-bottomed flask, mixing and heating at 40° C. for about 30 minutes, and removing the solvent under reduced pressure on a rotary evaporator. Solid and semisolid products were dried in an unheated vacuum oven for 4–6 hours to remove residual methanol to provided the controlled release compositions.

The solid compositions were then evaluated using (1) the salt water leaching test as described in Example 3 and the relative release test (5-day) described in Example 2. A summary of the performance of the three inorganic carriers (diatomaceous earth, aluminosilicate and magnesium silicate) relative to the carbon-based adsorbent (activated carbon) composition of the present invention is presented in Table 4.

TABLE 4

% 4,5-Dichloro-2-n-octyl-3-isothiazolone Retention

| Carrier Type | Paint Type | 5 Day % Released | Salt Water Leaching Test (28 Days) (% Retained in Paint Film) |
|---|---|---|---|
| None | P-1 | — | 64 |
| C-1 | P-1 | — | 91 |
| C-4* | P-1 | — | 80 |
| C-5* | P-1 | — | 75 |
| C-6* | P-1 | — | 73 |
| None | None | 100 | — |
| C-1 | None | 37 | — |
| C-4* | None | 55 | — |
| C-5* | None | 62 | — |
| C-6* | None | 85 | — |

\*comparative

Solid compositions using inorganic carriers (diatomaceous earth, aluminosilicate and magnesium silicate) release 4,5-dichloro-2-n-octyl-3-isothiazolone too quickly relative to the carbon-based adsorbent composition (C-1) of the present invention, based on either the short-term release test (5-day) or the long-term (28-day) salt water leaching test. For example, the C-4, C-5 and C-6 compositions only retain 15–45% 4,5-dichloro-2-n-octyl-3-isothiazolone versus 0% with no carrier (5-day surfactant solution) and only 73–80% 4,5-dichloro-2-n-octyl-3-isothiazolone versus 64% with no carrier (28-day salt water). In contrast, the carbon-based adsorbent composition (C-1) retains greater than 60% and greater than 90% 4,5-dichloro-2-n-octyl-3-isothiazolone, respectively.

We claim:
1. A non-aqueous liquid composition comprising a 3-isothiazolone compound having low water solubility; a high surface area activated carbon; and an organic solvent carrier, wherein the composition provides controlled release of the 3-isothiazolone compound, wherein the weight ratio of 3-isothiazolone compound to activated carbon is from 0.1:99.9 to 95:5, and wherein the activated carbon is a particulate material having an average particle size of 30 to 150 microns.

2. The composition of claim 1 wherein the 3-isothiazolone compound is represented by formula I:

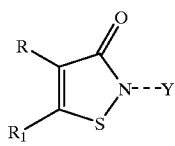

(I)

wherein:
Y is an unsubstituted or substituted ($C_7$–$C_{18}$)alkyl group, an unsubstituted or substituted ($C_7$–$C_{18}$)alkenyl or alkynyl group, an unsubstituted or substituted ($C_7$–$C_{12}$) cycloalkyl group, an unsubstituted or substituted ($C_7$–$C_{10}$)aralkyl group, or a substituted ($C_7$–$C_{10}$)aryl group;

R and $R_1$ are independently hydrogen, halogen, ($C_1$–$C_4$) alkyl groups or R and $R_1$ combine with the C=C double bond of the isothiazolone ring to form an unsubstituted or substituted benzene ring.

3. The composition of claim 2 wherein the 3-isothiazolone compound is selected from one or more of 2-n-octyl-3-isothiazolone, 4,5-dichloro-2-n-octyl-3-isothiazolone, 4,5-dichloro-2-benzyl-3-isothiazolone and 2-benzyl-3-isothiazolone.

4. The composition of claim 1 wherein the organic solvent carrier is selected from one or more of acetonitrile, ethyl acetate, butyl acetate, toluene, xylene, methanol, ethanol, acetone, methyl ethyl ketone, methyl isobutyl ketone, methyl isoamyl ketone, ethylene glycol, diethylene glycol, propylene glycol and dipropylene glycol.

5. A method for controlling the growth of bacteria, fungi, algae and marine fouling organisms comprising introducing to a locus to be protected the composition of claim 1.

6. The method of claim 5 wherein the locus to be protected is selected from cooling towers, air washers, mineral slurries, pulp and paper processing fluids, paper coatings, swimming pools, spas, adhesives, caulks, mastics, sealants, agriculture adjuvant preservation, construction products, cosmetics and toiletries, shampoos, disinfectants and antiseptics, formulated industrial and consumer products, soaps, laundry rinse waters, leather and leather products, wood products, plastics, lubricants, hydraulic fluids, medical devices, metalworking fluids, emulsions and dispersions, paints, varnishes, latexes, odor control fluids, coatings, petroleum processing fluids, fuel, oil field fluids, photographic chemicals, printing fluids, sanitizers, detergents, textiles, textile products and marine structures.

7. The method of claim 6 wherein the locus to be protected is selected from one or more of paints, coatings and marine structures.

8. A method for controlling the growth of bacteria, fungi, algae and marine fouling organisms comprising introducing to a locus to be protected:
(a) a high surface area activated carbon;
(b) a low water solubility 3-isothiazolone compound as represented by formula I:

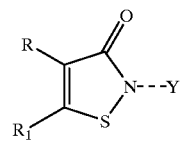

(I)

wherein:
Y is an unsubstituted or substituted ($C_7$–$C_{18}$)alkyl group, an unsubstituted or substituted ($C_7$–$C_{18}$)alkenyl or alkynyl group, an unsubstituted or substituted ($C_7$–$C_{12}$) cycloalkyl group, an unsubstituted or substituted ($C_7$–$C_{10}$)aralkyl group, or a substituted ($C_7$–$C_{10}$)aryl group:

R and $R_1$ are independently hydrogen, halogen, ($C_1$–$C_4$) alkyl groups or R and $R_1$ combine with the C=C double bond of the isothiazolone ring to form an unsubstituted or substituted benzene ring; and (c) an organic solvent carrier;
wherein the weight ratio of 3-isothiazolone compound to activated carbon is from 0.1:99.9 to 95:5, and wherein the activated carbon is a particulate material having an average particle size of 30 to 150 microns.

9. The composition of claim 3 wherein the weight ratio is from 5:95 to 30:70.

10. The method of claim 6 wherein the marine structure is selected from one or more of boats, ships, oil platforms, piers, pilings, docks, elastomeric rubbers and fish nets.

* * * * *